US012658303B2

(12) United States Patent
Alves Ferreira et al.

(10) Patent No.: US 12,658,303 B2
(45) Date of Patent: Jun. 16, 2026

(54) METHOD AND SYSTEM FOR GENERATING PHYSICAL ACTIVITY RECOMMENDATIONS AND NON-TRANSITORY COMPUTER READABLE STORAGE MEDIUM

(71) Applicant: SAMSUNG ELETRÔNICA DA AMAZÔNIA LTDA., Campinas (BR)

(72) Inventors: Leonardo Alves Ferreira, Campinas (BR); Julio Cesar Mendoza Bobadilla, Campinas (BR); André Zanon, Campinas (BR); Greice Cristina Mariano, Campinas (BR); Rafael Akihiro Matumoto, Campinas (BR); Gyovana Mayara Moriyama, Campinas (BR); Maira Suzuka Kudo, Campinas (BR); Desiree Camara Miraldo, Campinas (BR); Luiz Miguel Cerqueira, Campinas (BR); Pedro Manoel Cesar Moreira, Campinas (BR); Luz Albany Arcila Castaño, Campinas (BR); Paula Ramos Pinto, Campinas (BR); Jinmook Lim, Suwon-si (KR); Hyun Gi Ahn, Suwon-si (KR); DongHyun Roh, Suwon-si (KR); Kyungsub Min, Suwon-si (KR)

(73) Assignee: SAMSUNG ELETRÔNICA DA AMAZÔNIA LTDA., Campinas (BR)

( * ) Notice: Subject to any disclaimer, the term of this patent is extended or adjusted under 35 U.S.C. 154(b) by 113 days.

(21) Appl. No.: 18/594,327

(22) Filed: Mar. 4, 2024

(65) Prior Publication Data

US 2025/0226077 A1     Jul. 10, 2025

(30) Foreign Application Priority Data

Jan. 8, 2024     (BR) ........................ 10 2024 0002989

(51) Int. Cl.
| | | |
|---|---|---|
| *G16H 20/30* | (2018.01) | |
| *A61B 5/00* | (2006.01) | |

(Continued)

(52) U.S. Cl.
CPC ............ *G16H 20/30* (2018.01); *A61B 5/1118* (2013.01); *A61B 5/7264* (2013.01); *A61B 5/74* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 7,717,827 | B2 | 5/2010 | Kurunmaki et al. |
| 10,255,823 | B2 | 4/2019 | Jang et al. |

(Continued)

FOREIGN PATENT DOCUMENTS

| | | |
|---|---|---|
| CN | 101668482 A | 3/2010 |
| CN | 109529303 B | 3/2021 |

(Continued)

OTHER PUBLICATIONS

Bakrania, K., Edwardson, C.L., Bodicoat, D.H. et al. Associations of mutually exclusive categories of physical activity and sedentary time with markers of cardiometabolic health in English adults: a cross-sectional analysis of the Health Survey for England. BMC Public Health 16, 25 (2015) (Year: 2015).*

(Continued)

*Primary Examiner* — Devin C Hein
*Assistant Examiner* — Vincent C Ilagan
(74) *Attorney, Agent, or Firm* — STAAS & HALSEY LLP

(57) ABSTRACT

A method of generating physical activity recommendations comprising: calculating an active time and a moderate time based on user historical data comprising data of physical (Continued)

activities of a user, the active time representing an amount of time of physical activities with any intensity that the user performed in a period of analysis and the moderate time representing an the amount of time of physical activities with an intensity higher than a predetermined threshold performed by the user during the period of analysis. The method includes calculating a user state representing a current amount of physical activities performed by the user in the period of analysis; and determining a goal recommendation for a subsequent period and a target amount of physical activity, wherein the goal recommendation comprises a goal for the active time and a goal for the moderate time to increase, decrease or maintain the amount of physical activities.

21 Claims, 5 Drawing Sheets

(51) Int. Cl.
 *A61B 5/11* (2006.01)
 *G16H 10/60* (2018.01)

(56) References Cited

U.S. PATENT DOCUMENTS

| | | | | |
|---|---|---|---|---|
| 2005/0172311 | A1* | 8/2005 | Hjelt | A63B 69/0028 |
| | | | | 725/12 |
| 2017/0291067 | A1* | 10/2017 | Jang | G09B 19/0092 |
| 2020/0179757 | A1 | 6/2020 | Toivonen et al. | |
| 2020/0215299 | A1* | 7/2020 | Myllymäki | A61B 5/4815 |
| 2023/0138673 | A1* | 5/2023 | Crawford | G16H 20/10 |
| | | | | 600/365 |
| 2023/0252909 | A1* | 8/2023 | McNair | G09B 19/00 |
| | | | | 434/236 |

FOREIGN PATENT DOCUMENTS

| | | | | |
|---|---|---|---|---|
| WO | WO2015069124 A1 | 5/2015 | | |
| WO | WO-2017032635 A1 * | 3/2017 | | A61B 5/1118 |

OTHER PUBLICATIONS

Coolbaugh C, Raymond Jr S, Hawkins D, "Feasibility of a Dynamic Web Guidance Approach for Personalized Physical Activity Prescription Based on Daily Information From Wearable Technology," JMIR Res Protoc 2015;4(2):e67 (Year: 2015).*

Trella, AL.; Zhang, K.W.; Nahum-Shani, I.; Shetty, V.; Doshi-Velez, F.; Murphy, S.A. Designing Reinforcement Learning Algorithms for Digital Interventions: Pre-Implementation Guidelines. Algorithms 2022, 15, 255. (Year: 2022).*

Tudor-Locke, C., Craig, C. L., Brown, W.J. et al. How many steps/day are enough? for adults. Int J Behav Nutr Phys Act 8, 79 (2011). https://doi.org/10.1186/1479-5868-8-79 (Year: 2011).*

Hu X, Hsueh P, Chen C, et al. "An interpretable health behavioral intervention policy for mobile device users," IBM J. Res. & Dev., vol. 62, No. 1, Paper 4, pp. 1-10, Jan.-Feb. 2018. (Year: 2018).*

American College of Sports Medicine. "ACSM's guidelines for exercise testing and prescription". Wolters Kluwer: 11th ed., Chapter 5 and 6 (partial), 2021.

World Health Organization. "WHO guidelines on physical activity and sedentary behavior: web annex: evidence profiles." (2020).

Ekelund, Ulf, et al. "Dose-response associations between accelerometry measured physical activity and sedentary time and all-cause mortality: systematic review and harmonized meta-analysis." bmj 366 (2019).

Piercy, Katrina L., et al. "The physical activity guidelines for Americans." Jama 320.19 (2018): 2020-2028.

Jetté, M. et al., "Metabolic equivalents (METS) in exercise testing, exercise prescription, and evaluation of functional capacity." Clinical cardiology 13.8 (1990): 555-565.

Support Apple. https://support.apple.com/en-us/HT212501. Access in Jun. 23, 2023.

Google Fit Help. Available in https://support.google.com/fit/answer/7619539?hl=en&co=GENIE.Platform%3DAndroid#zippy=%2Cbased-on-your-heart-rate. Access in Jun. 23, 2023.

Mujika, Iñigo, and Sabino Padilla. "Cardiorespiratory and metabolic characteristics of detraining in humans" Medicine & Science in Sports & Exercise 33.3 (2001): 413-421.

U.S. Department of Health and Human Services (2018). Physical Activity Guidelines Advisory Committee Scientific Report, 2018.

U.S. Department of Health and Human Services (2008). Physical Activity Guidelines Advisory Committee Report, 2008.

Bakrania, K. et al., (2015)."Associations of mutually exclusive categories of physical activity and sedentary time with markers of cardiometabolic health in English adults: a cross-sectional analysis of the Health Survey for England" BMC public health, 16, 1-10.

Who, O. (2020). "WHO guidelines on physical activity and sedentary behaviour" Geneva: World Health Organization.

Ekelund, Ulf et al. Joint associations of accelerometer-measured physical activity and sedentary time with all-cause mortality: a harmonised meta-analysis in more than 44 000 middle-aged and older individuals. British journal of sports medicine, v. 54, n. 24, p. 1499-1506, 2020.

* cited by examiner

1

METHOD AND SYSTEM FOR GENERATING PHYSICAL ACTIVITY RECOMMENDATIONS AND NON-TRANSITORY COMPUTER READABLE STORAGE MEDIUM

CROSS-REFERENCE TO RELATED APPLICATION(S)

This application is based on and claims priority under 35 U.S.C. § 119 to Brazilian Patent Application No. BR 102024000298-9, filed Jan. 8, 2024, in the Brazilian Intellectual Property Office, the disclosure of which is incorporated by reference herein in its entirety.

FIELD OF THE DISCLOSURE

The present invention refers to a method for generating personalized recommendations to user in order to increase moderate-to-vigorous physical activity and reduce sedentary activity behavior using data collected by wearable devices.

DESCRIPTION OF RELATED ART

The inclusion of physical activities (PA) in the daily routine can have many benefits. WHO [1] and ACSM [2] state that performing 150 to 300 minutes of moderate-to-vigorous physical activity (MVPA) in the week provides many benefits, such as: reduction of all-cause mortality and cardiovascular disease mortality, as well as a reduced risk of hypertension, diabetes, colon cancer and breast cancer.

In addition to performing MVPA, increasing the quantity of movements in the daily life with PA of any intensity is another beneficial action a person could take, since it reduces the amount of time spent being sedentary. In that regard, reducing the amount of sedentary behavior can decrease the all-cause mortality risk even for people that already performs MVPA during the week [3].

However, current international guidelines do not describe how the person should achieve the goal of reducing sedentary time. As a result, there is a possibility of a person achieving the MVPA goal but spending the remaining time of the week performing sedentary behaviors, which could result in health risks. Therefore, increasing the daily amount of active time is also important. Differently from MVPA time, active time takes into account PA of any intensity.

The intensity of a PA is related to the effort a person needs to exert to perform an activity, and it can be classified as light, moderate or vigorous. Light PA includes activities where the heart or breathing rate is not substantially increased, such as slow walking [4]. In comparison, an example of moderate PA would be brisk walking, while vigorous PA includes jogging or running [4].

A more accurate way to estimate PA intensity is by the heart rate zones. These zones are defined based on the ratio between the current heart rate of a person and their Maximal Heart Rate ($HR_{max}$). The estimation of the ($HR_{max}$) of a person can be obtained by subtracting the person's age from 220. Equations (1) and (2) bellow illustrate the $HR_{max}$ and PA intensity equations, respectively, in which age is the person's current age in years and HR is a heart rate record measured during a PA.

$$HR_{max}(\text{age}) = 220 - \text{age} \qquad (1)$$

2

-continued $$\text{Intensity}(HR, \text{age}) = \frac{HR}{HR_{max}(\text{age})}100 \qquad (2)$$

ACSM [2] states that when Equation (2) results in a value between 57 and 63%, the person is performing a light PA; when it is between 64 and 76%, the person is performing a moderate PA; and when it is between 77 and 95% the person is performing a vigorous PA. Furthermore, ACSM [2] and WHO [1] also define the intensity of a PA based on an energy expenditure measure named as Metabolic Equivalent (MET). MET is the ratio between the energy that a person spends during an activity and the energy that a person spends while sitting quietly [5], as described by Equation (3). In this equation, $\text{Energy}_{activity}$ is the energy a person spends during the activity and $\text{Energy}_{sitting}$ is the amount of energy spent while seated at rest.

$$MET = \frac{\text{Energy}_{activity}}{\text{Energy}_{sitting}} \qquad (3)$$

Using this measure, a sedentary activity is defined as an activity performed at a value less than or equal to 1.5 MET [4]. Other PA intensities are defined as:

Light-intensity, an activity performed at 1.5 to 2.9 METs.

Moderate-intensity, an activity performed at 3 to 5.9 METs.

Vigorous-intensity, an activity performed at ≥6 METs.

Based on this scenario, our solution is a personalized coaching that could be a feature of a wearable device, such as a smart-ring, a smartwatch, a smart-band or similar devices containing the necessary sensors to detect movement and classify PA intensity. The solution aims at monitoring the MVPA and active time of a user and at generating personalized recommendations to improve these quantities. These objectives are achieved through the analysis of the user's behavior throughout the coaching program and by adapting goals of MVPA and active time based on it.

The proposed approach has the main objective of safely improving the user MVPA and active time by following international guidelines [1, 2, 4]. In order to achieve this objective, it is important to determine how much PA the user currently performs, how much to increase the PA duration, and for which domain to prioritize the increase (MVPA or active time). As a result, the proposed method provides an increment to MVPA or to active time every week, considering the user's current behavior and past PA duration and intensity.

The method is aligned with the principles of PA progression and prescription. These principles include: the overload, which means challenging the current fitness/performance of the person by increasing the PA recommendation; the progression, which defines that the PA can be increased by changing frequency, duration, intensity or type of the activity; and individualization, which states that the modification of the recommendations should be changed based on the user capacity and their response to the PA.

If a person is highly sedentary, the WHO's [1] guideline recommends to gradually add light PA to their routine, which can be achieved by recommending active time goals; when the person achieves a sufficient level of active time, MVPA goals can be recommended to increase the intensity of the PA the person is doing, leading to additional health benefits. In that regard, increments should also be personalized considering the user's behavior, meaning, for example, that if the user is failing to achieve the goals, the increments should be decreased. Conversely, if the user is increasing their PA time faster than the increments, the system could also provide larger increments, limited by the safety recommendations stated by international guidelines [2, 4]. Furthermore, current scientific evidence [1] recognizes that any increase in PA is beneficial to health for a sedentary person, which means that if the user prefers increasing active time over MPVA time, the system should allow this behavior.

Our method takes into account this information to provide personalized PA recommendations, meaning that it automatically changes the strategy to determine the goals considering the user's behavior. It is different from competitors whose approach provides a static objective that does not change over the weeks. The Apple Fitness [7], for instance, considers a static objective in calories set by the user. Google Heart Points [8], although aligned with the same guidelines, does not provide automatic and personalized objectives to the user. Furthermore, our approach differs from competitors by providing two goals for the user to achieve: MVPA and active time. Besides taking into account a more complete scenario of the user's PA behavior, having these two goals allow for different recommendation strategies that can be adapted to the user's preference. In conclusion, the system has the potential to improve users' health with a more individualized approach in comparison with competitors, helping users to achieve international guidelines of MVPA and active time.

Currently, simplistic approaches to recommending PA consists of providing constant values of goals and/or increments based on health guidelines recommendations. Below we present a summarized description of the encountered related art and the key differences to our solution.

The patent "U.S. Pat. No. 7,717,827B2—Method and system for controlling training", by Firstbeat Analytics Oy, introduces a method to provide personalized PA recommendations based on a database of workout templates created by health specialists. The user is classified into an Activity Class based on the previous 28 days of PA. The classification considers duration, frequency and load of the exercises performed in the past. Based on the Activity Class and the user's physiological aim (e.g., lose weight, increase endurance), the adequate training level of the template is selected. The template defines sessions of exercise, which are specified based on the training effect (variable that combines duration and intensity). Each training level has a target range of training effect. If the user is below or above the recommended range, the training effect of the following days are adjusted accordingly so the user returns to the range. The template and the user's preference define the days of the week the sessions are recommended. The user can progress to a different training level after at least 28 days following the recommendations of the current level. In the new level, duration, frequency and/or intensity are increased. The recommended exercise duration between consecutive training levels can have a difference of more than 100 minutes. Different from this method, our solution gradually increases the recommendations every week based on the user pace and executed activity. Also, our solution also considers the option of increasing the duration of light activities to obtain health benefits.

The document "WO2015069124A1—Automated prescription of activity based on physical activity data", by Performance Lab Technologies Limited, describes a method to prescribe and modify workouts based on physiological and performance variables. The workout is composed of different types of activity based on the intensity, speed and vertical meters climbed. The method creates a workout plan alternating types of activity with different durations. The plan is modified based on the measurements about user performance and physiological state. The modifications include increasing, decreasing or cancelling types of activity from the workout. For example, if fatigue is detected during a workout, the remaining activities may be cancelled. On the other hand, if the algorithm identifies that the strength endurance increased by a predefined percentage, the duration of some activities may be extended in the following workouts. Our method is different from this solution because it describes an alternative way to recommend physical activities that is more flexible and focus on the fact that any type of increase in the PA is beneficial to health.

The patent "US20200179757A1—Method, an apparatus and a software product for providing a training program", by Firstbeat Analytics Oy, presents a method to personalize exercise programs based on user activity and training goal. This method is an extension of U.S. Pat. No. 7,717,827B2, which proposes an alternative that dismisses the use of a database of workout templates. The exercise programs are based on a predefined plan that is composed of cycles alternating easy, medium and hard physical activities. After determining the user's activity class from his/her past activity history, the application sets training goals to progressively increase the activity class. This solution establishes the progression based on a predefined template and imposes different intensities of training, therefore differing from our method that adapts the goals according to the user's pace and response.

The patent "U.S. Ser. No. 10/255,823B2—Method and apparatus for generating personalized exercise program", by Samsung Electronics Co Ltd, introduces a method that determines personalized MET information for the user. This information is used to prescribe activities that will result in the user expending the desired amount of energy throughout the day. The amount of energy is determined based on the training goal and on guidelines or calorie intake. Different from our solution, this method does not specify a strategy to perform the progression of the PA recommendations.

The patent "CN101668482A—Activity measurement system", by Matsushita Electric Works Ltd, presents a system for measuring amount of activity. After determining the amount of daily activity and exercise activity from the user's past activity history measured using the sensor of the mobile device, the system classifies the user's activity type and provides personalized recommended goals for both exercise and daily activities. While exercise goals are calculated based on exercise intensity above a reference threshold, daily activity goals are based on activity intensity and caloric consumption below the reference threshold. Differently from our solution, in this method the goals are completely independent from each other, so the exercise is not considered as a daily activity.

The patent "CN109529303B—User movement capacity confirmation method and system", by Shenzhen Quantum Intelligent Technology Co Ltd, presents a method and a system for confirming user exercise ability using a wearable device and then, set a safe exercise plan. The safe exercise plan is based on heart rate zones for fatigue recovery, which means that the plan is based on safe ranges that mitigate cardiovascular risks. In contrast, our solution defines safe ranges that prevents musculoskeletal injuries by limiting increments between weeks in a row.

The paper entitled "Building a Personalized Fitness Recommendation Application based on Sequential Information"

presents a method that provides PA recommendations based on heart rate, speed and altitude of the user while exercising. To determine the thresholds used in the recommendations, a clustering technique was applied to a dataset of exercise records. The technique resulted in five groups of people. The values of the variables in each group determined the safe thresholds to be used in the recommendations. Initially, the user is classified into one of the five groups and a recommendation of the safe range of heart rate while exercising is produced based this information. Then, the user is monitored during the exercise and if any of the evaluated variables exceeds the safe threshold, a warning is produced recommending an action to reduce risks. This idea relates to our solution because it also provides PA recommendations according to a user classification. However, the classification the method uses is solely based on data analysis, while ours uses information from health guidelines and scientific literature.

The paper entitled "Dynamic Physical Activity Recommendation Delivered through a Mobile Fitness App" introduces a method that uses clustering algorithms to generate personalized PA recommendations. Two clustering stages are executed on a dataset. In the first, clusters are formed based on physiological and PA features. Each group obtained in the first stage is further clustered according to the period of each day of the week when the person performs the activity. Based on the user classification and on the activity patterns, a model predicts an activity plan to recommend for the user. Additionally, the accumulated amount of activity is used to predict if the user will complete the daily goal in the remaining time of the day. If the model predicts the user will not complete the goal, the goal is adjusted accordingly. This paper also uses a user classification method to define PA recommendations, but the classification is based on data, while our classification is mostly based on health guidelines and scientific literature.

The book entitled "Be he@lthy, be mobile: a handbook on how to implement mobile health for physical activity" presents a series of recommendations to be followed when designing digital approaches to promote PA. Additionally, the book describes a behavior change program with the aim of motivating people to achieve the WHO's recommendation of 150 minutes of MVPA per week. The program defines a schedule of messages to be sent during a 4-6 week period containing goals and relevant tips and information. The messages content and quantity are based on behavior change theory. Therefore, similar to our solution, the program uses motivational messages and goals to help users to achieve the WHO's recommendation. However, different from our method, the program described on the book does not consider any personalization in the setting and progression of the goals. The goals and increments between weeks are fixed and are not adapted according to user compliance to the recommendations.

As seen above, the state of the art comprises different solutions related to recommendations of physical activities. However, these approaches do not consider methods to personalize the progression and goals based on the users' actions after receiving the recommendations, nor they present strategies to handle failure to achieve the goals. More elaborate methods use as basis for the recommendations predefined workout templates created by health experts, which contains sessions with specific variables as: frequency, durations, intensities and/or types of exercise.

Therefore, these methods prioritize the experience of the consulted health experts instead of incorporating consensual information present in health guidelines or consolidated scientific literature; and are targeted at people willing to follow a more rigid exercise regimen. In addition, these solutions only handle user failure by adjusting the recommendations so the user can follow the initial workout template or by providing an easier version of the template, without alternative strategies that could be followed to obtain health benefits, as we propose.

Another important consideration is that most of the methods encountered in the related art do not include any consideration regarding the importance of reducing sedentary time, which is found to be relevant even for people who already practice MVPA.

SUMMARY OF THE INVENTION

The present invention includes a method of generating physical activity recommendations, the method comprising: calculating an active time and a moderate time based on user historical data comprising data of physical activities of a user, the active time representing an amount of time of physical activities with any intensity that the user performed in a period of analysis and the moderate time representing an amount of time of physical activities with an intensity higher than a predetermined threshold performed by the user during the period of analysis; calculating a user state representing a current amount of physical activities performed by the user in the period of analysis with basis on the active time and the moderate time; and determining a goal recommendation for a subsequent period based on the user state and a target amount of physical activity, wherein the goal recommendation comprises a goal for the active time and a goal for the moderate time to increase, decrease or maintain the amount of physical activities.

In addition, the present invention also refers to a system for generating physical activities recommendations comprising a memory and a processor configured to perform the method for generating physical activity recommendations.

The present invention is also related to a non-transitory computer-readable storage medium for performing the method for generating physical activity recommendations.

BRIEF DESCRIPTION OF THE DRAWINGS

The invention is explained in greater detail below and references the drawings and figures attached herewith, when necessary. Attached herewith are the following.

DETAILED DESCRIPTION OF THE INVENTION

Figure 1:
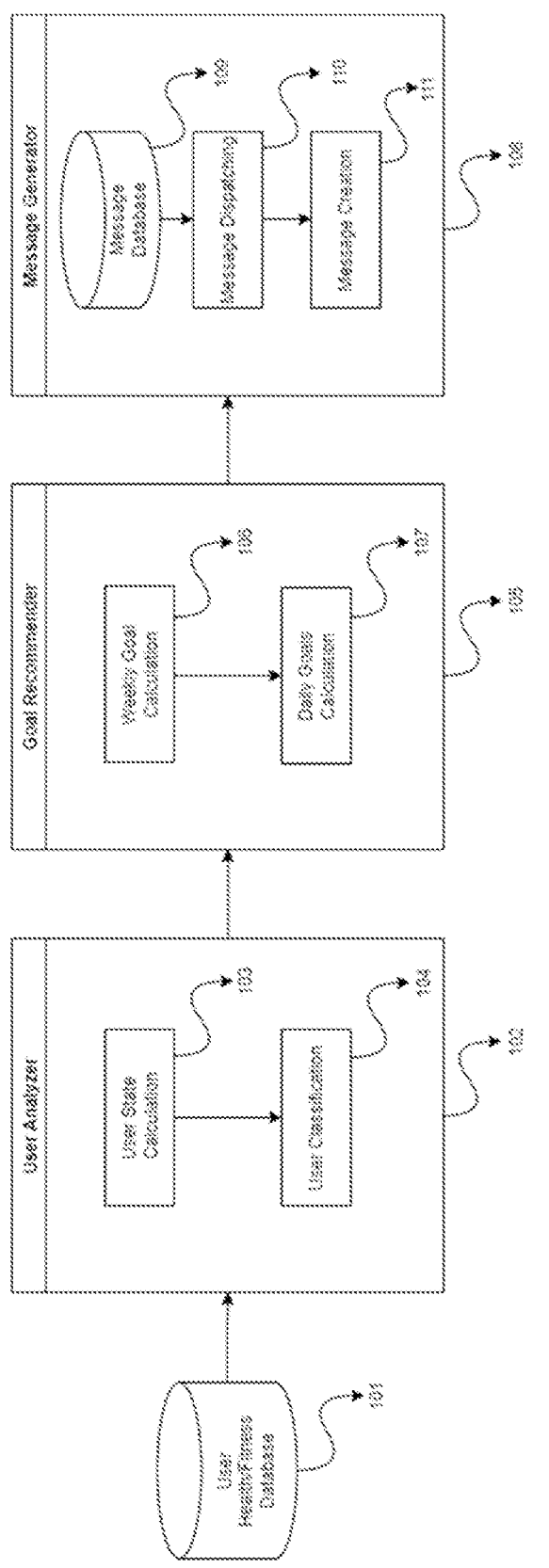
FIG. 1 shows an overview of the proposed solution according to an embodiment of the present invention.

The present invention refers to a method for generating physical activity recommendations, the method comprising:

calculating an active time and a moderate time based on user historical data comprising data of physical activities of the user, wherein the active time represents the amount of time of physical activities with any intensity that the user performed in a period of analysis and the moderate time represents the amount of time of physical activities with an intensity higher than a predetermined threshold performed by the user during the period of analysis;

calculating a user state representing the current amount of physical activities performed by the user in the period of analysis with basis on the active time and the moderate time; and determining a goal recommendation for a subsequent period based on the user state and a target amount of physical activity, wherein the goal recommendation comprises a goal for the active time and a goal for the moderate time to increase, decrease or maintain the amount of physical activities.

Generally, the purpose of this invention is to generate personalized PA recommendations by following guidelines of exercise prescription and training progression as well as by taking into account user data. The data considered in this method include information about the user's movement and heart rate (HR), collected throughout the day by any wearable device, such as smartwatches, smart-bands and smart-rings.

The method combines recommendations to increase MVPA and to reduce sedentary behavior (increase active time) until reaching an adequate amount of PA to reduce mortality risk. As an example, the recommendation, provided by WHO, of a value equivalent to 300 minutes of moderate PA (3 MET) in the week, can be used as the final MVPA goal. In the case of active time, current scientific literature points out that the hazard bought by daily sedentary time occurs for people spending more than 8 hours in this behavior per day [7]. In other words, the benefits obtained by reducing sedentary time further than 8 hours per day is not well-established. Based on this information, the final active time goal should correspond to spending 8 hours per day being sedentary. If we consider that the user will use the sensor device at least 12 hours per day and that the sensor device records the active time of the user accurately, the active time corresponding to 8 hours of sedentary time is 4 hours. Alternatively, different limit values can be obtained considering the estimation error of the sedentary time from the active time recorded by the sensor device. Based on these examples, the final active time goal requires a total of 1680 minutes in the week, while the final MVPA goal requires 300 minutes or less (if the user performs activities at an intensity greater than 3 MET).

In each week, the recommendations prioritize the increase either of the MVPA goal or of the active time goal, which we name as primary goal, while instructing the user to at least maintain the current level of the other, which we name as secondary goal. To decide the preferred strategy, the users are classified in one of seven types based on the current level of both goals. The strategy comprises the definition of the PA component to be prioritized as the primary goal and, consequently, the PA component to be defined as secondary goal. In addition, the strategy also defines a suggestion regarding how to achieve the primary goal, which has as consequence a tendency to maintain, to increase or to avoid increasing the secondary goal (due to risky factors or to the lack of evidence regarding the benefits of further increasing it).

If the method detects that the user is consistently failing to follow the preferred strategy in a predetermined period of time, the strategy is changed to experiment if a different approach is better for the user. For example, the active time goal may be easier for people who have enough free time and have difficulty exercising at higher intensities. In contrast, the MVPA goal may be easier for people who have little time available. Therefore, the method allows the users to increase their PA with the approach that is best suited to them.

The increment added to the user's current level of PA, to generate the weekly goals, is calculated each week based on an estimate of the progression rate of the user. The estimate is obtained from a regression model fitted to the user history data. In addition, the increment is limited to be within a range defined according to health literature information regarding safe and beneficial increment values between consecutive weeks of an exercise progression.

The weekly goals are distributed equally throughout the week to generate the daily goals. If the user under or overachieve the goal, the daily goals of the following days are adjusted accordingly so the recommendations lead to the achievement of the weekly goal at the end of the week. This way, the user can use different distributions of PA to achieve the weekly goal, which is in accordance with current scientific knowledge. Also, the redistribution of the daily goals is capped when the method detects that further increasing them may be unsafe or not beneficial, according to a rationale based on the health literature.

Our solution lets users to select a mode of use in which the goals are calculated aiming at maintaining the current user state. In order to do that, our solution defines maintenance goals based on the user state in the moment of enabling the maintenance mode. Moreover, our solution adapts the strategies in order to guide the users to achieve the maintenance goals when their PA decreases. Finally, the user can get back to the normal mode of use. In that scenario, the strategies return to its initial definition. As consequence, the user starts receiving increments in the weekly goal until reaching the Busy Bee type or until enabling the maintenance mode again.

The method includes the generation of messages to instruct the user about the goal and recommended strategy. The messages also comprise cases that handle user behavior that is not aligned with the recommendations of the method. In these cases, beneficial actions are encouraged or congratulated regardless, while risky behaviors are warned.

In the related art, there is no approach that combined recommendations of both MVPA and active time (or sedentary time). In addition, related approaches handle user failure by adjusting the goals so the user can still achieve the initial recommendation, or by providing an easier version of the same recommendation. In comparison, ours presents two different possibilities of increasing PA that are recommended according to the user current level of activity and compliance to the recommendations.

The proposed solution, as shown in FIG. 1, is designed to receive and analyze health and fitness data (101) from the user, preferably acquired with sensor device that could be a wearable device such as a smart-ring, a smartwatch, a smart-band or another similar device. Based on health and fitness data of users (101), the user analyzer module (102) calculates the current amount of PA of the user, which we named as user state (103), and classifies the user to determine the best progression strategy (104) to generate the recommendation for the user to achieve the target amount of PA. Then, the goal recommender module (105) calculates the weekly (106) and daily goals (107) of the user based on the user state and the progression strategy. Finally, the message generator module (108) receives the user and context information, determines when a message should be dispatched (110) and what message template (109) should be used to create recommendation (111) messages. Finally, the message is shown to the user through the application device.

User Analyzer Module

Figure 2:
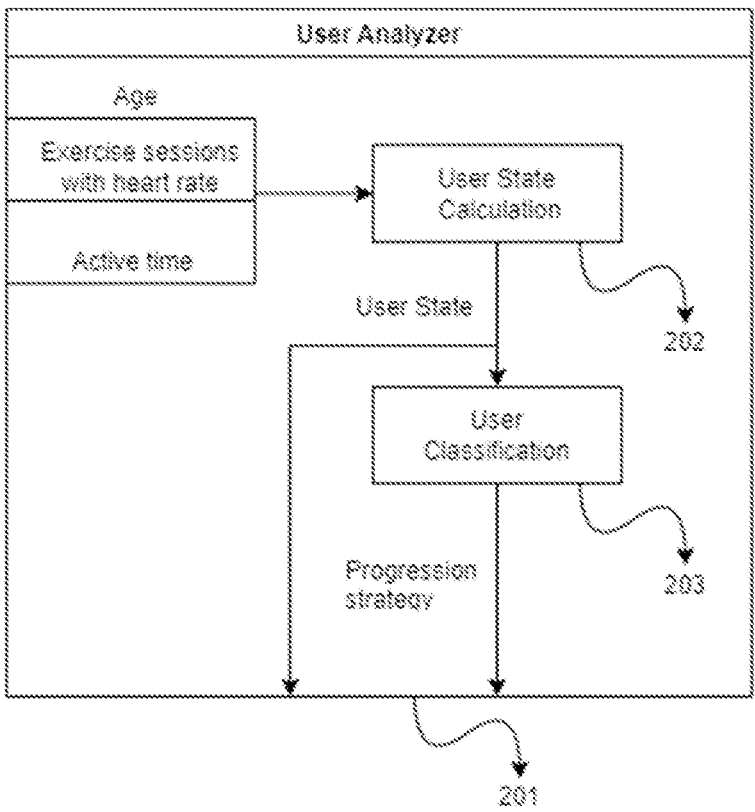
FIG. 2 shows with more details the components of the user analyze module according to an embodiment of the present invention.

We show an overview of the user analyzer module (201) in FIG. 2. The user analyzer module has a method to calculate the user state (202) and a method to classify the users and determine the best progression strategy to guide the users to increase their PA based on the classification (203).

The user state is used to determine the best progression strategy for the user, and to determine the PA goals that will be delivered to the user through the recommendation messages.

Since our solution is designed to recommend active time and MVPA time goals, the user state is composed of an active time component and an MVPA component. As an example, the active time component of the user state is expressed in terms of the average active time per day in the week, whereas the MVPA time component is expressed as the total amount of moderate time (at 3 MET) in the week. Therefore, the user state component related to MVPA is obtained by converting the MVPA time into moderate intensity PA at 3 MET. The reason for the intensity conversion to 3 MET is that one key principle of the proposed solution is to deliver safe recommendation messages to users, hence the PA recommended by our solution is at most at the lowest moderate intensity. From this point forward, we refer to the MVPA time as moderate time, meaning the equivalent amount of activity performed at 3 MET, obtained through the conversion.

The components of the user state are determined once a week, at the beginning of every week. To determine the value of each component, we use a method that analyzes the user historical data of a predetermined period of time, e.g., the last 4 weeks. We refer to this period as period of analysis.

For each component, the method determines the component of the user state by analyzing the PA related to this component and comparing what was done in the last week with what was done in the period of analysis. If the user performed a high amount of PA in the last week with respect to the period of analysis, the user state component is defined as the amount of PA from the last week. Therefore, in this situation the weekly goal is computed considering the PA of the last week.

If the user did a low amount of PA related to the component in the last week with respect to the period of analysis, the component of the user state is determined as a summary statistic of the PA in the weeks of the period of analysis. Therefore, the user state decreases slower than the PA the user performed. A slow decrease in the user state components is consistent with the observation that the capacity to exercise decreases slowly through time when the person performs less PA [9]. Also, this mechanism helps to avoid the situation where the user loses their user state progress due to an external factor, such as an unusually busy schedule in the week.

The condition to determine if the user did a high or low PA related to the component in the last week with respect to the period of analysis is verifying if the last week's PA related to the component is greater or equal to a summary statistic of the amount of PA in the weeks of the period of analysis. If this condition is true, our method considers that the user has a high PA related to the component in the last week with respect to the period of analysis. Otherwise, our method considers that the user has a low PA related to the component.

An unsafe situation could result from the user exceeding the goals and increasing the amount of PA too fast between consecutive weeks. The method that determines the user state addresses this scenario by limiting the possible increment of the user state components between consecutive weeks. This way, if the user is increasing the PA too fast, the method will determine a lower user state to encourage a slower and safer pace. Therefore, the determination of a component $U_i$ of the user state on week i is given by Equation (4):

$$U_i = \min(\mathrm{Act}_{sup}, \max(H_{i-1}, f_{stat}(H_{i-1}, H_{i-2}, \dots , H_{i-n}))) \tag{4}$$

where $\mathrm{Act}_{sup}$ is a safe weekly limit for the increment of the component, based on current health recommendations, $f_{stat}(\bullet)$ is a function representing a summary statistic, and $H_i$ is the PA performed by the user on week i for the component, and n is the number of weeks in the period of analysis.

As a preferred embodiment, we use a period of analysis of 4 weeks. Ideally, this period should not be too small, to avoid instability of the user state, nor too big, to avoid the user from regressing to a user state from a long time in the past. As a preferred summary statistic we use the median, since it is more robust to outliers in the data.

Regarding the preferred embodiment for defining $\mathrm{Act}_{sup}$, we define the safe ranges for the weekly increment of moderate time considering two key statements: (1) guidelines recommend spreading aerobic PA on at least 3 days to produce health benefits and to help reducing the risk of injury and excessive fatigue [11], and (2) guidelines suggest adding between 5 to 15 minutes of light-to-moderate PA per session every week [11]. The extreme case scenario complying with the first statement is when the user spreads the weekly moderate time goal on 3 days of the week, 1 session per day. Based on the second statement, the range of safe increments in this scenario is from $\mathrm{inc}_{inf}=15$ to $\mathrm{inc}_{sup}=45$ minutes/week for the moderate time. The method uses this safe range for all users to ensure safe recommendations. We consider the same guidelines to define the safe range for active time, which we define as being from $\mathrm{inc}_{inf}=5$ to $\mathrm{inc}_{sup}$, $=15$ minutes/day in the preferred embodiment.

To determine the best progression strategy, we use a method that receives the user state and classifies the user into one of seven user types. The method assigns a different progression strategy based on the user type. Each progression strategy describes a primary and a secondary weekly goal. The primary goal is defined as a numeric goal of active time or moderate time that is increased every week based on historical data of the user. The secondary goal is provided as a numeric goal of active time or moderate time that has the same value as the corresponding component of the current user state of the user or is a predefined limit. In addition, each type defines a textual suggestion on how to increase the primary goal, which may have an impact on the user state component related to the secondary goal. The impact may result in the user maintaining, increasing, or avoiding increasing the component related to the secondary goal. We show in FIG. 3 the user types.

Inspired by a study that analyzed PA behavior considering a two-dimensional space defined by the MVPA time and the sedentary time [12], we created four major types for the users of the solution based on the active time and the moderate time. This classification is defined by a threshold value $T_1$ of moderate time and a threshold value $T_2$ of active time. The value of $T_1$ indicates the recommended amount of moderate time a person should achieve in the week to lower their mortality risk without a significant risk of injury or excessive fatigue. As an example, we chose $T_1$ as the current WHO recommendation, for healthy adults, of 300 minutes of moderate PA in the week.

The value of $T_2$ indicates a sufficient amount of active time in the week to mitigate the hazard caused by sedentary behaviors. Current scientific evidence indicates that the hazard brought by daily sedentary time occurs for people spending more than 8 hours in this behavior [13]. In other words, the benefits obtained by reducing sedentary time to less than 8 hours per day is not well-established. Therefore, $T_2$ should reflect a reduction of sedentary time to 8 hours per day. As an example, by assuming a device wear time of 12 hours, $T_2$ would be chosen as 240 minutes.

Figure 3:
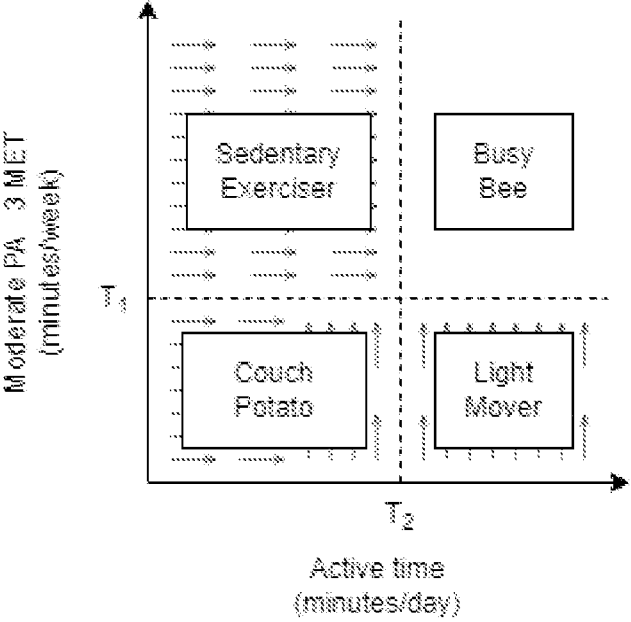
FIG. 3 illustrates the four major user types with their respective primary goals according to an embodiment of the present invention.

Based on these thresholds, we defined the four major types. FIG. 3 shows the four major user types and their primary goal strategies, which are indicated by the direction of the arrows.

Sedentary exerciser refers to users that have a user state with at least $T_1$ minutes/week of moderate time and less than $T_2$ minutes/day of active time. Therefore, the user achieved the recommended goal of moderate PA but still has a high amount of sedentary behavior in their routine. Sedentary exerciser users receive as primary goal an increased value of their current active time, and as secondary goal the same value of their current moderate time. The suggestion associated with this type is to achieve the primary goal by adding light PA to the routine, therefore maintaining the same moderate time. In addition, the suggestion includes a warning to be careful about adding more moderate time to their routine, since increasing it further than $T_1$ minutes/week could lead to an increased risk of musculoskeletal injury and fatigue [13].

Light mover: These users have a user state with less than $T_1$ minutes/week of moderate time and at least $T_2$ minutes/day of active time. Therefore, the user has a low sedentary time, but still needs to do more MVPA to obtain more health benefits. Light mover users receive as primary goal an increased value of their current moderate time and as secondary goal the value of $T_2$ minutes/day of active time. The suggestion associated with this type is to achieve the primary goal by increasing, to moderate, the intensity of the light PA they are already performing, therefore maintaining their current active time. In addition, the suggestion includes a warning that adding more light PA to their routine is not as beneficial as before, since their sedentary time is already low enough.

Busy bee: These users have a user state with at least $T_1$ minutes/week of moderate time and at least $T_2$ mins/day of active time. These users achieved the final objective of both moderate and active time. Therefore, busy bee users receive a recommendation to maintain the same moderate time they are already doing and to maintain $T_2$ mins/day of active time.

Couch potato: These users have a user state with less than the equivalent of $T_1$ minutes/week of moderate time and less than $T_2$ minutes/day of active time. Therefore, these users did not achieve any of the final objectives intended by the method. In order to add more personalization, we subdivided this type into four subtypes to define different strategies of progression.

Similarly, to the major types, we considered two thresholds to subdivide the Coach potato user type: $T_3$ of moderate time and $T_4$ of active time. We defined $T_3$ as a value that indicates more advanced users of the coaching program, meaning that they are accustomed to adding more moderate PA to their routine. As an example, we use the guideline [2] information that, after successfully following an exercise program for a week, an inactive person can start to receive more advanced recommendations. Based on this information, and on the previous example that defined the minimum increment of moderate time between consecutive weeks as $inc_{inf}$=15 minutes, the value of $T_3$ is defined as 60 minutes of moderate time. This is the value a person, starting from 0 minutes/week of moderate time, would reach after successfully achieving the goals provided by the method during a month.

We defined $T_4$ as a value that indicates a high hazard caused by sedentary behavior. Although there exists evidence showing that the hazard becomes significant after 8 hours of sedentary time per day, this evidence also shows that the risk continues to increase with additional time spent in this behavior. Additional evidence [14] indicates that the mortality risk originated from sedentary behavior can be mitigated by performing MVPA. However, for a high enough sedentary time, even achieving the MVPA recommendation provided by WHO may not be sufficient to totally mitigate the risk [14]. $T_4$ is chosen to correspond to this high amount of sedentary time.

As an example, we chose the value of $T_4$ based on an analysis of the data presented in [14], which shows the joint association between total MVPA, sedentary time and all-cause mortality. Based on this analysis, we observed that when the sedentary time is higher than 10.7 hours/day, the higher value of mortality risk is statistically significant even when the amount of moderate PA performed is equal to 300 minutes per week. Therefore, we chose $T_4$ to correspond to this value. Following a rationale similar to what was explained for $T_2$, this information results in a $T_4$ of 78 minutes of active time per day.

Figure 4:
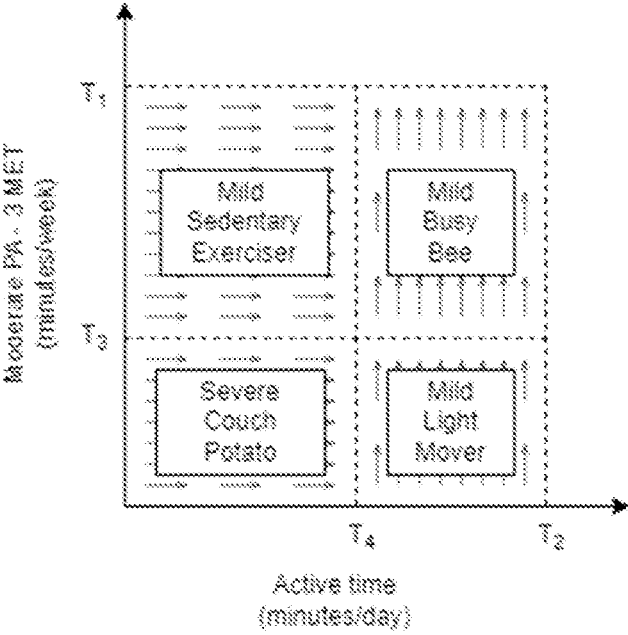
FIG. 4 illustrates the four types originated from the coach potato type subdivision and their primary goals according to an embodiment of the present invention.
Figure 5:
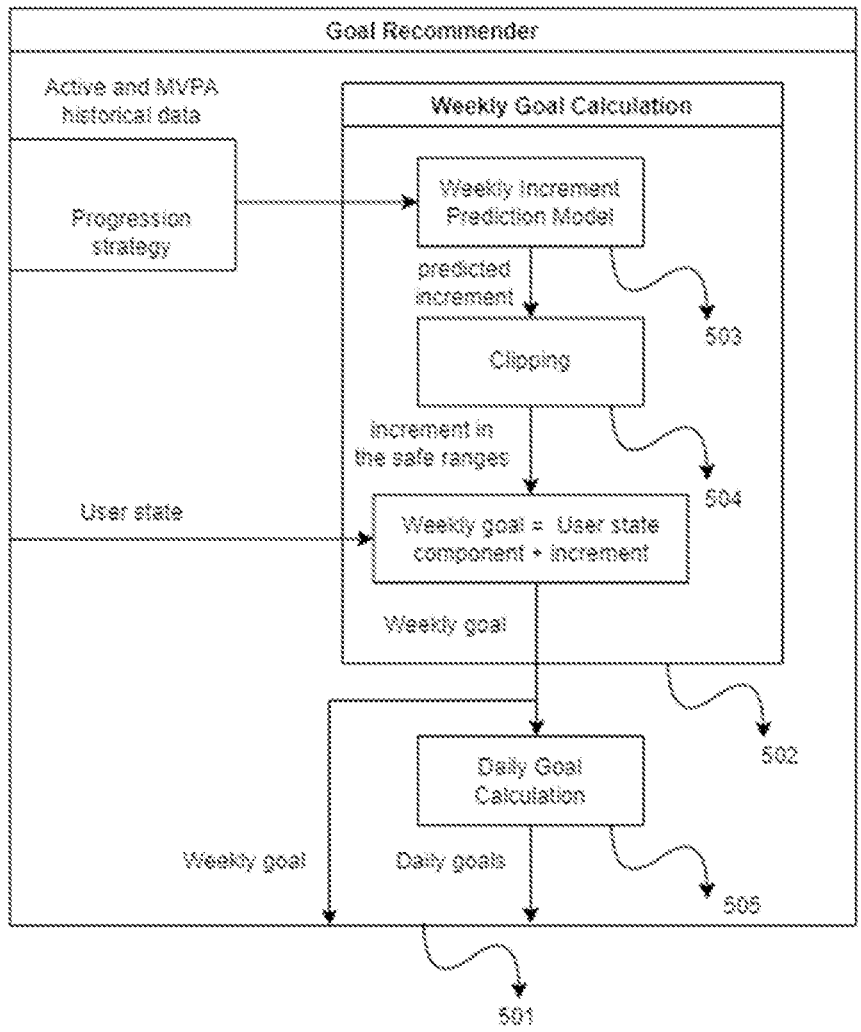
FIG. 5 shows with more detailed the components of the goal recommender module according to an embodiment of the present invention.

Based on both these thresholds, we subdivide the coach potato user type in four user types. We show the coach potato types and their primary goal strategies, indicated by the direction of the arrows, in FIG. 4.

Severe Coach Potato: These users have a moderate time below $T_3$ and an active time below $T_4$. Therefore, these users have a high value of sedentary time and a low amount of moderate PA in their routine. Severe couch potato users receive as primary goal an increased value of their current active time and no value of moderate time for the secondary goal. Since these users are extremely inactive, the solution recommends the user to add light PA to their routine to achieve the primary goal, which is in accordance with guidelines recommendations [4]. For the same reason, the secondary goal, which is the moderate time in this case, is not considered in this type.

Mild Sedentary Exerciser: These users have a Moderate time equal or above $T_3$ and an Active time below $T_4$. Therefore, these users are more accustomed to adding moderate PA to their routine, but still spend a high amount of time in sedentary behavior. Mild sedentary exercise users receive as primary goal an increased value of their active time and as secondary goal the same value of their current moderate time. Since these users are more advanced, the suggestion in this type is that the user can combine light and moderate PA to achieve the primary goal. Consequently, the suggestion guides the user to maintain or also increase their moderate time.

Mild Light Mover: These users have a moderate time below $T_2$ and an active time equal or above $T_1$. Therefore, these users already reduced the mortality risk associated to sedentary behavior, but still have a very low amount of moderate PA in their routine. Mild light mover users receive as primary goal an increased value of their current moderate time and as secondary goal the same value of their current active time. Since these users are not advanced yet, the suggestion for this type is for the user to increase the intensity of the light PA they are doing to moderate intensity, thus not needing to add more PA to their routine. Consequently, the suggestion guides the user to maintain the same active time.

Mild Busy Bee: These users have reached both $T_3$ and $T_4$. Since performing MVPA is the most well-established way to reduce mortality risk [13], mild busy bee users receive as primary goal an increased value of their current moderate time and as secondary goal the same value of their current active time. Since these users are more advanced, the suggestion for this type is that the users can also add new PA of moderate intensity to their routine, in addition to the activities they are already doing. Consequently, the suggestion guides the user to maintain or also increase the active time.

Although we defined a preferred path for the Coach Potato recommendations according to the subtypes, other paths are possible and would benefit the user health. Therefore, the method also includes a mechanism to modify the aforementioned strategies. The strategy is changed when the method detects that the user is persistently failing to increase the time of the primary goal during a predetermined period of m-weeks, for example the last 4 weeks. The failure is determined as follows: let $A=\{1, 2, \ldots, m\}$ be the set of the week's indexes of the considered period, $H_i$ the PA value recorded on week i for the primary goal, and $\varepsilon_{diff}$ a tolerance value. Then, a failure is detected when, for every value $i \in A$, we have that $H_i < (H_j + \varepsilon_{diff})$ for every value $j < i$ and $j \in A$. The tolerance $\varepsilon_{diff}$ is a small value included to add robustness to the method by disregarding small variations in the PA duration.

As an example, if the historical data of a mild light mover meets the failure condition, the primary goal of the recommendations becomes increasing their active time. This way, if the user is having difficulty increasing their moderate time, they can still continue to increase their active time to achieve the health benefits of reducing sedentary behavior. The new strategy is maintained while the user continues in the same type or while a new failure is not detected.

Goal Recommender

The goal recommender (501) module is composed by a method that estimates the weekly goal (502) and by a method that distributes the weekly goal into daily goals (505). The main principles for this module's logic were that the recommendations should be safe and adaptable to the pace of the user progression. Additionally, the goal recommender module determines the weekly and daily goals in active time or moderate time depending on what is the current primary goal.

As explained previously, we defined safe ranges for the increments of PA duration between consecutive weeks based on [10]. The smallest ($inc_{inf}$) and largest ($inc_{sup}$) values for these ranges were from 5 to 15 minutes for active time, and from 15 to 45 minutes for moderate time (3 MET). Regardless of the user's activity history, the increment determined by the goal recommender is clipped to be within these ranges. Additionally, for users without a history, the increment is initialized as the minimum value of the safe range.

When the activity history is available, the method responsible for estimating the weekly goal (502) considers the active time and moderate time data from a predetermined period of t-weeks, aiming at capturing the current tendency of the user regarding the execution of PA.

The weekly goal increment is estimated by fitting a regression model in the user's historical data, such as a simple linear regression model, an artificial neural network, or another regression model. As an example, we fit a simple linear regression model (503)($H^{model}(w_0, w_1, i)=w_1 i+w_0$, where i represents the week index) to the users data. Once this model is fitted, we define the personalized increment as the slope coefficient ($inc_{per}=w_1$) of the resulting line.

The personalized increment is clipped ($inc_{safe}=\max(\min (inc_{per}, inc_{inf}), inc_{sup})$) in the safe range (504) and used as the increment determined by the goal recommender. This way, if the user is increasing the PA duration in a pace different from the increase rate of the recommendations, the method adapts to better follow the user's behavior (as long as it is considered safe).

Once the increment is determined, the goal recommender defines the weekly goal as the sum of the component of user state related to the primary goal and the increment ($inc_{safe}$). This operation is executed once per week. Then the goal recommender distributes the weekly goal into daily goals (505). The method responsible for calculating the daily goals (505) distributes the weekly goal equally between the seven days of the week. The rationale behind this decision is that the maximum daily goal of the week is the minimum possible, favoring the perception that the goals are achievable. However, current scientific literature establishes that different distributions of the PA throughout the week can be used to achieve health benefits [2]. The current recommendation is that the PA should be distributed into at least three days to reduce the risk of injuries and fatigue.

Based on these observations, the method that calculates the daily goals (505) redistributes them to allow for different distributions of the PA. This method comprises calculating the difference between the daily goal and the activity the user performed during the day, and then equally distributing this difference throughout the remaining days of the week. Therefore, if the user exceeds the daily goal, a proportional quantity is subtracted from the goals of the following days. Conversely, if the daily goal is not met, the remaining time is equally divided and added to the following days. Alternatively, the method that calculates the daily goals ($day_i$) can redistribute them calculating the difference of the weekly goal (W) and amount of PA performed in the week until the current day ($P_i$) and equally distributing this difference throughout the remaining days of the week $$\left(day_i = \max\left(0, \frac{W - P_i}{8 - i}\right)\right).$$

Both explained procedures have the same outcome.

To ensure the safety of this redistribution, the goal recommender limits the amount of moderate time the daily goals can reach. This limit is based on the recommendation of distributing the PA into at least three days of the week. Expressly, the limit is defined as one third of the weekly goal $$\left(day_{sup} = \frac{W}{3}\right)$$

and is used to cap the redistribution of the daily goals $$\left(\text{day}_i^{(safe)} = \min\!\left(\text{day}_i,\, \text{day}_{sup}\right)\right).$$

In the case of active time, the benefits obtained by reducing sedentary time further than 8 hours per day is not well-established [13]. As explained before, this value of sedentary time may be associated to a value of 4 hours of active time. Therefore, in this example, the goal recommender limit the redistribution to a maximum of 4 hours per day ($\text{day}_{sup}$=240). The rationale behind our logic to determine the active time limit value is to avoid recommending goals to the user that have insufficient evidence demonstrating they will lead to significant health benefits.

Users might not be able to achieve the final goals of moderate time ($T_1$) or active time ($T_2$). Therefore, we provide to them the option of manually selecting a mode of use where the goals are calculated aiming at maintaining the current user state. We refer to this mode of use as "maintenance mode" and to the normal mode of use as "progression mode".

In order to guide the user to maintain their current physical activity, our method defines maintenance goals $AT_m$, for active time, and $MT_m$, for moderate time. The maintenance goals are defined when the user selects the maintenance mode. The values of the maintenance goals are determined as the values of the current user state of the user, which was defined at the beginning of the current week. A special case occurs in the Light Mover type, where the active time goal is limited to the value of $T_2$. While in this mode, the user is guided to maintain the values $AT_m$ and $MT_m$. Even if the user performs more than these values, the goals are clipped to be at maximum $AT_m$ and $MT_m$.

In the week that the user enables the maintenance mode, the method updates the primary weekly goal to the value of the corresponding maintenance goal. Then, the method redistributes the weekly goal into daily goals the same way as in the progression mode, taking into account the amount of physical activity the user already performed in the current week.

In the following weeks, if the user state components are below their respective maintenance goals, the normal rules of the progression mode are used to guide the user back to achieve these goals. If the user state component related to the current primary goal is greater than or equal to its respective maintenance goal, and if the user state component related to the secondary goal is less than its respective maintenance goal, then a change of strategy is applied to the current user type, similar to what happens when a persistent failure to increase PA is detected.

Consequently, the progression strategy is changed to increase the PA time related to the maintenance goal that the user did not achieve yet. For example, if the condition to change the strategy is met and if the progression strategy of the current user type has as primary goal to increase moderate time, then the primary goal is changed to increase active time. This change is maintained while the user does not meet another criteria to change strategy again or while they do not achieve both the maintenance goals.

The user can get back to the progression mode. When the user enables the progression mode, the method guides the user to achieve the final goals required to reach the Busy Bee type ($T_1$ and $T_2$) using the normal rules and the initial strategies of the user types. The weekly and daily goals do not change during the week where the progression mode is enabled. In the following weeks, the weekly goal starts receiving increments according to the strategies until the user reaches the Busy Bee type or until they enable the maintenance mode again.

Message Generator

The message generator module is responsible for defining the messages to be sent to the user, as well as for establishing the conditions in which to send each message. The message's main purpose is to inform users about their recommendations. In addition, the content of the messages is aimed at motivating the achievement of the goals and suggesting possible actions.

Four message categories were created to handle different situations.

A recommendation aimed at informing the value of the primary goal the user should achieve and suggest the strategy to be used for that. In addition, it also includes recommendations about the secondary goal and one or more examples of PA that could be performed. This category comprises the weekly goals, sent at the beginning of each week, and the daily goals, sent at the beginning of each day.

A reminder aimed at reminding the user that the goal, or part of it, still needs to be achieved. This category includes at most one message per day, sent when the user did not complete the daily goal by a specified time, such as the beginning of the evening.

A modification aimed at handling cases where the user did not follow the recommendation. This category includes, for example, warning users about risky behaviors, such as exercising beyond what is recommended by health guidelines; suggestions to choose the maintenance mode of use and explanations about strategy changes when the primary goal is not being successfully achieved. With this category, the message generator is able to adapt to different user behaviors and provide adequate content even when the recommendations are not being followed.

A reward aimed at congratulating the user on achieving the weekly and daily goals. Messages of this category are sent even if the user exceeded the goals, as long as the exceeding amount do not poses a health risky according to the maximum safe increment determined by the other modules. Moreover, the user is also congratulated on increasing their PA, even if they did not achieve the goals completely, and are encouraged to reach the next goals. In addition, this message category comprises suggestions to change to the progression mode of use when the user is in the maintenance mode and is achieving the goals in consecutive weeks. These messages are sent at the end of the day.

Figure 6:
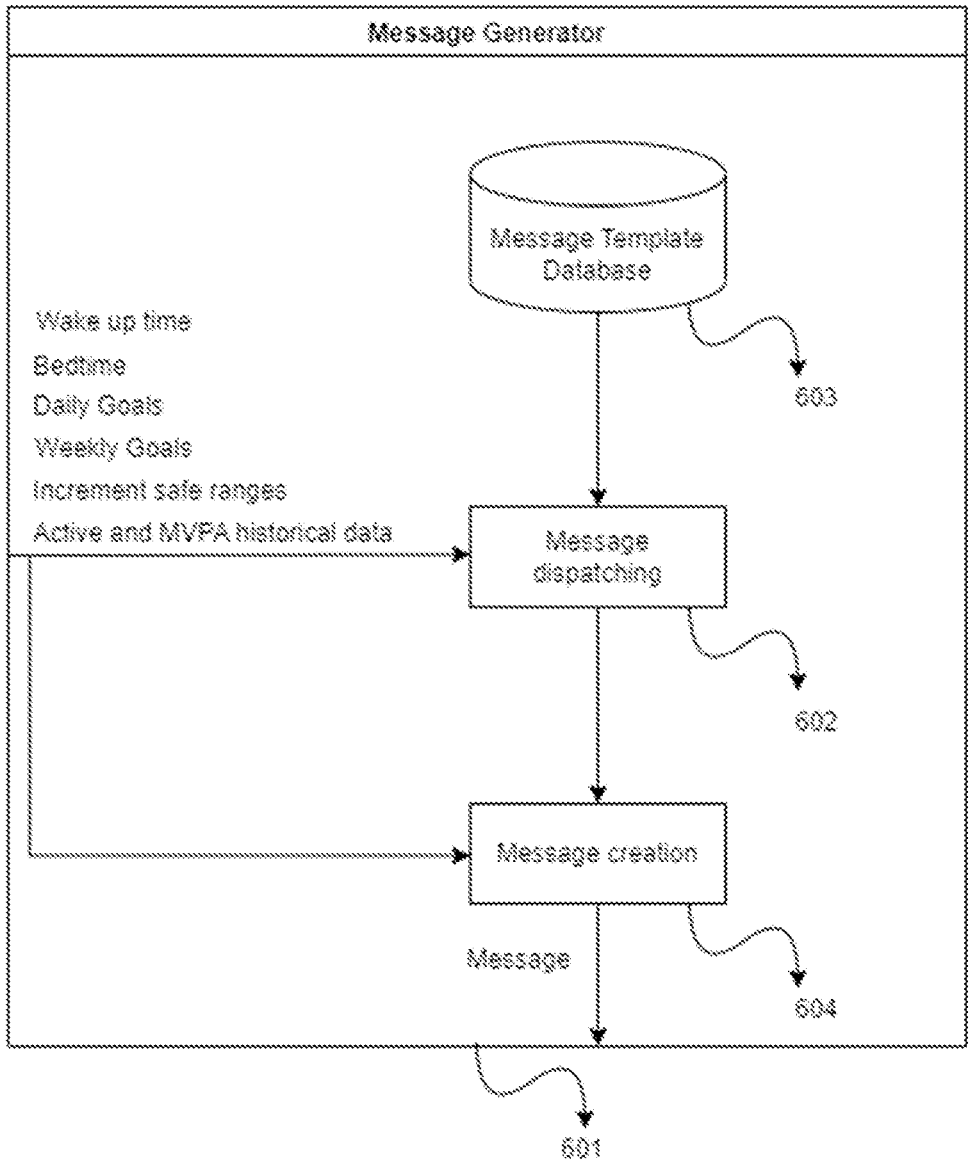
FIG. 6 depicts an instance of the message generator module according to an embodiment of the present invention.

FIG. 6 depicts an instantiation of the message generator module (601). This module has a database of message templates (603) of the four message categories that are used to create the messages. The message generator module has a method that determines when a message should be created and dispatched to the user (602). The message dispatching method has a set of conditions to deal with different possibilities of user behavior, reinforcing any alternative action considered safe and beneficial, as well as warning about risky behaviors. The message generator module receives user information such as wake up time, bed time, active time historical data, MVPA time historical data; the daily goals and weekly goals; and context information such as the current time and date. Based on the received information, the message dispatching method determines when a message should be dispatched and selects what template will be used to create the message that will be shared to the user. Then, the message creation method (604) receives the message template and the user context information, and create the message. Finally, the message is shared with the user through the device application.

Alternative Embodiments

In the first embodiment, we take into account variables related to sedentary time (active time) and moderate time.

In a second embodiment, other fitness-related variables could also be included, such as variables related to resistance training and flexibility. The methods proposed here could be extended to accommodate these additional goals. For example, health guidelines related to resistance training could be used to establish progressive goals of load and repetitions. Information regarding the new variables would be recorded in the user historical data. Then, the user state would have additional components related to each new variable. Every week, the person would have one primary goal and multiple secondary goals. In other words, every week the person would be guided to improve one of the components while at least maintaining their progress for the others. This way, the person would have specific guidance for other possibilities of improving their health, according to their preferences. The disadvantage of this embodiment when compared to the first embodiment is that it could require manual inputs from the user, such as the type of exercise and number of repetitions and sets performed, or a set of sensors to monitor different body parts. In contrast, in the first embodiment we only include variables that could be easily monitored by common wearables such as physical activity duration and heart rate.

In a third embodiment, the Busy Bee type is extended to include new types for people aiming at more advanced goals, such as training for a marathon or other sport-related activities where the progression of the duration is a key factor. In this method, the person that achieves the Busy Bee type receives the option to maintain their current status or to specialize into a more advanced type. This way, people that are more athletic would be able to continue to use the methods of progression to achieve their objective. A drawback of this embodiment is that it includes riskier activities, which may require the user to consult with a health professional for evaluation and additional guidance.

In the first embodiment, the method that calculates the user state components switches between the last and a summary statistic of the component values in the weeks of the period of analysis of active or MVPA time depending on the pattern of the period of analysis. A fourth embodiment could consider a single summary statistic such as the median, the mean, or another statistic to determine the value of one or both components of the user state. The drawback of this approach is that the user would progress in a slower pace, since the method would always consider the whole period of analysis.

In a fifth embodiment, a different rule of change of strategy is used for the maintenance mode when the user state component associated with the primary goal is equal to or greater than its corresponding maintenance goal and the secondary goal is lower than its corresponding maintenance goal. In this embodiment, the change of strategy is only maintained while the user state associated with the original primary goal of the current user type is equal to or greater than its corresponding maintenance goal. Therefore, if this user state component is reduced, the strategy is changed back to its original definition. The disadvantage of this embodiment when compared to the preferred embodiment is that it may favor a greater number of changes of the definition of the primary goal because a small decrease in the user state component may be enough to trigger this condition.

Moreover, the proposed solution communicates the goals to the user through the recommendation messages. Thus, alternative embodiments can be derived by considering the recommendation message and a subset of the other message categories: reminder, modification, and reward messages. For example, a simpler embodiment could be obtained by just considering the recommendation and reward messages. This approach would have the benefit of reducing the number of messages the user receives, but with the risk of not providing enough motivation for the users to complete their goals.

Effect

As seen above, our solution describes a flexible and adaptable method to recommend PA and limit sedentary behavior. The main purpose is to motivate users to adopt a healthier routine to reduce mortality risk. To achieve this objective, an important aspect of the method was to create mechanisms to adapt the recommendations according to the user behavior, especially aiming to encourage the goal achievement of users that are failing.

The solution includes an innovative approach to classify users according to the amount of MVPA they perform and the daily sedentary time they accumulate. This classification is used to establish the preferred strategy to produce the recommendations. The recommendations are based on health guidelines and scientific evidence to ensure their safety and beneficial effects. The rate of progression between consecutive weeks is adjusted according to the user pace, and alternative strategies are used to produce recommendations if the user is failing to achieve the goals.

Therefore, by providing multiple types of scientific-based recommendations that are flexible to the user preferences and behavior, it is expected that our approach will reach a broader public than existing methods, motivating the users to improve the MVPA quantity and reduce the amount of time they spend in sedentary behavior. The solution is computationally lightweight and can be applied to any combination of a smartphone and a wearable capable of monitoring body movement and heart rate, such as smartwatches or smart rings.

In addition, as it will be clear for a person skilled in the exemplificative embodiments described herein may be implemented using hardware, software, or any combination thereof and may be implemented in one or more computer systems or other processing systems. Additionally, one or more of the steps described in the example embodiments herein may be implemented, at least in part, by machines. Examples of machines that may be useful for performing the operations of the example embodiments herein include general purpose digital computers, client computers, portable computers, mobile communication devices, tablets, smartphones, notebooks or wearable electronic devices, such as smartwatches.

For instance, one illustrative example system for performing the operations of the embodiments herein may include one or more components, such as one or more microprocessors, for performing the arithmetic and/or logical operations required for program execution, and storage media, such as one or more disk drives or memory cards (e.g., flash memory) for program and data storage, and random-access memory, for temporary data and program instruction storage.

Therefore, the present invention is also related to a system for generating physical activity recommendations comprising a processor and a memory comprising the computer-readable instructions that, when performed by the processor, cause the processor to perform the method steps previously described in this disclosure.

The system may also include software resident on a storage media (e.g., a disk drive or memory card), which, when executed, directs the microprocessor(s) in performing transmission and reception functions. The software may run on an operating system stored on the storage media, such as, for example, UNIX or Windows, Linux, Android, and the like, and can adhere to various protocols such as the Ethernet, ATM, TCP/IP protocols and/or other connection or connectionless protocols.

As well known in the art, microprocessors can run different operating systems and contain different software types, each type being devoted to a different function, such as handling and managing data/information from a particular source or transforming data/information from one format into another format. The embodiments described herein are not to be construed as being limited for use with any particular type of server computer, and any other suitable device for facilitating the exchange and storage of information may be employed instead.

Software embodiments of the illustrative example embodiments presented herein may be provided as a computer program product or software that may include an article of manufacture on a machine-accessible or non-transitory computer-readable medium (also referred to as "machine-readable medium") having instructions. The instructions on the machine-accessible or machine-readable medium may be used to program a computer system or other electronic device. The machine-readable medium may include, but is not limited to, floppy diskettes, optical disks, CD-ROMs, magneto-optical disks, or another type of media/machine-readable medium suitable for storing or transmitting electronic instructions.

Therefore, the present invention also relates to a non-transitory computer-readable storage medium for generating physical activity recommendations, comprising computer-readable instructions that, when performed by the processor, cause the processor to perform the method steps previously described in this disclosure.

The techniques described herein are not limited to any particular software configuration. They may be applicable in any computing or processing environment. The terms "machine-accessible medium," "machine-readable medium" and "computer-readable medium" used herein shall include any non-transitory medium that is capable of storing, encoding, or transmitting a sequence of instructions for execution by the machine (e.g., a CPU or other type of processing device) and that cause the machine to perform any one of the methods described herein. Furthermore, it is common in the art to speak of software in one form or another (e.g., program, procedure, process, application, module, unit, logic, and so on) as taking action or causing a result. Such expressions are merely a shorthand way of stating that the execution of the software by a processing system causes the processor to act to produce a result.

While various exemplary embodiments have been described above, it should be understood that they have been presented by example, not limitation. It is apparent to persons skilled in the relevant art(s) that various changes in form and detail can be made therein.

REFERENCES

[1] World Health Organization. "WHO guidelines on physical activity and sedentary behavior: web annex: evidence profiles." (2020).

[2] American College of Sports Medicine. "ACSM's guidelines for exercise testing and prescription". Wolters Kluwer: 11th ed., 2021.

[3] Ekelund, Ulf, et al. "Dose-response associations between accelerometry measured physical activity and sedentary time and all-cause mortality: systematic review and harmonized meta-analysis." bmj 366 (2019).

[4] Piercy, Katrina L., et al. "The physical activity guidelines for Americans." Jama 320.19 (2018): 2020-2028.

[5] Jetté, Maurice, Ken Sidney, and G. Blümchen. "Metabolic equivalents (METS) in exercise testing, exercise prescription, and evaluation of functional capacity." Clinical cardiology 13.8 (1990): 555-565.

[7] Support Apple. https://support.apple.com/en-us/HT212501. Access in 23/06/2023.

[8] Google Fit Help. Available in https://support.google.com/fit/answer/7619539?hl=en&co=GENIE.Platform%3DAndroid #zippy=%2Cbased-on-your-heart-rate. Access in 23/06/2023

[9] Mujika, Iñigo, and Sabino Padilla. "Cardiorespiratory and metabolic characteristics of detraining in humans." Medicine & Science in Sports & Exercise 33.3 (2001): 413-421.

[10] U.S. Department of Health and Human Services (2018). Physical Activity Guidelines Advisory Committee Scientific Report, 2018.

[11] U.S. Department of Health and Human Services (2008). Physical Activity Guidelines Advisory Committee Report, 2008.

[12] Bakrania, K., Edwardson, C. L., Bodicoat, D. H., Esliger, D. W., Gill, J. M., Kazi, A., . . . & Yates, T. (2015). Associations of mutually exclusive categories of physical activity and sedentary time with markers of cardiometabolic health in English adults: a cross-sectional analysis of the Health Survey for England. BMC public health, 16, 1-10.

[13] WHO, O. (2020). WHO guidelines on physical activity and sedentary behaviour. Geneva: World Health Organization.

[14] EKELUND, Ulf et al. Joint associations of accelerometer-measured physical activity and sedentary time with all-cause mortality: a harmonised meta-analysis in more than 44 000 middle-aged and older individuals. British journal of sports medicine, v. 54, n. 24, p. 1499-1506, 2020.

What is claimed is:

1. A computer implemented method of generating physical activity recommendations, the computer comprising a processor and a memory, the computer implemented method comprising:

calculating, by the processor, an active time and a moderate time based on user historical data which includes user historical movement and/or physiological data collected by means of movement and/or physiological sensors of a wearable device, wherein the user historical data comprises data of physical activities of a user, the active time representing an amount of time of physical activities with any intensity that the user performed in a period of analysis and the moderate time representing an amount of time of physical activities with an intensity higher than a predetermined threshold performed by the user during the period of analysis;

calculating, by the processor, a user state representing a current amount of physical activities performed by the user in the period of analysis with basis on the active time and the moderate time; and determining, by the processor, a goal recommendation for a subsequent period based on the user state and a target amount of physical activity, wherein the goal recommendation comprises a goal for the active time and a goal for the moderate time to increase, decrease or maintain the amount of physical activities;

wherein the period of analysis is defined by n weeks of the user historical data, wherein n is an integer number;

wherein the subsequent period is a week and the goal recommendation comprises a weekly goal for the subsequent period, and the method further comprises dividing the weekly goal into daily goals distributed along the subsequent period;

the method further comprising:

determining, by the processor, whether the user increased the amount of physical activities according to the weekly goal with an inequation $H_i \leq (H_j + \varepsilon_{diff})$ wherein $H_i$ is a physical activities value recorded on week i in a primary goal, $\varepsilon_{diff}$ is a tolerance value, wherein a failure is detected when, for every value $i \in A$, we have that $H_i \leq (H_j + \varepsilon_{diff})$ for every value j<i and $j \in A$, for A={1, 2, . . . , m}.

2. The computer implemented method according to claim 1, wherein the user historical data comprises physical activity data obtained from a sensor monitoring the user during physical activities sessions, the physical activity data comprising heart rate and movement data obtained by a wearable device.

3. The computer implemented method according to claim 2, further comprising:

classifying, by the processor, the user with basis on the active time and the moderate time with respect to a moderate time threshold value $T_1$ and an active time threshold value $T_2$;

wherein the user is classified as a sedentary exerciser based on the user state being at least $T_1$ of moderate time per week and less than $T_2$ of active time per day;

wherein the user is classified as a light mover based on the user state being less than $T_1$ of moderate time per week and at least $T_2$ of active time per day;

wherein the user is classified as a busy bee based on the user state being at least $T_1$ of moderate time per week and at least $T_2$ of active time per day; or wherein the user is classified as a couch potato based on the user state being less than $T_1$ of moderate time per week and less than $T_2$ of active time per day.

4. The computer implemented method according to claim 3, wherein in case the user is classified as couch potato, the method comprises further classifying the user with respect to a threshold active time $T_3$ and a threshold moderate time $T_4$, and wherein the user is classified as a severe couch potato based on user state is less than $T_3$ of moderate time per week and less than $T_4$ of active time per day;

wherein the user is classified as a mild sedentary exerciser based on the user state is between $T_3$ and $T_1$ of moderate time per week and less than $T_4$ of active time per day;

wherein the user is classified as a mild light mover based on the user state is less than $T_3$ of moderate time per week and between $T_4$ and $T_2$ of active time per day; or wherein the user is classified as a mild busy bee based on the user state is between $T_3$ and $T_1$ of moderate time per week and between $T_4$ and $T_2$ of active time per day.

5. The computer implemented method according to claim 1, wherein calculating the user state further comprises:

determining, by the processor, the active time and the moderate time by analyzing an associated physical activity and comparing physical activities registered in a period before the period of analysis with the physical activities in the period of analysis;

wherein based on the physical activity in a last week being higher than the physical activity in the period of analysis, the user state is defined as the amount of physical activities from the last week and a weekly goal is computed considering the physical activities of the last week; and based on the physical activity in the last week being less than the physical activities in the period of analysis, the user state is determined as a summary statistic of the physical activities performed during the period of analysis.

6. The computer implemented method according to claim 1, wherein determining the user state further comprises:

calculating, by the processor, the amount of physical activity that is considered to be safely performable by the user, $U_i$, wherein:

$$U_i = \min(\text{Act}_{sup}, \max(H_{i-1}, f_{stat}(H_{i-1}, H_{i-2}, \ldots, H_{i-n}))),$$

wherein $\text{Act}_{sup}$ is a predetermined value corresponding to a safe limit of progression between consecutive weeks determined by health recommendations, $f_{stat}(\bullet)$ is a summary statistic and $H_i$ is the physical activities performed by the user on a week i for the period of analysis.

7. The computer implemented method according to claim 6, wherein a weekly goal is determined as the current amount of physical activity that is considered to be safely performable by the user $U_i$ in addition to an increment $C_i$ based on the user historical data stored in a database, wherein $C_i$ is determined as $$C_i = \min(Inc_{sup}, \max(Inc_{inf}, inc_{per})),$$

wherein $Inc_{sup}$ and $Inc_{inf}$ are predetermined values based on health guidelines defining a safe and beneficial range of physical activity increments between consecutive weeks, and $inc_{per}$ is a regression model coefficient obtained by fitting the user historical data with a regression model.

8. The computer implemented method according to claim 7, wherein the regression model is one of a linear regression model or an artificial neural network.

9. The computer implemented method according to claim 8, wherein a weekly goal increment is estimated by a linear regression model defined by:

$$H^{model}(w_0, w_1, i) = w_1 i + w_0,$$

where i represents a week index to the user historical data; and, a personalized increment is defined as a slope coefficient $inc_{per} = w_1$ after fitting the linear regression model.

10. The computer implemented method according to claim 9, further comprising clipping, by the processor, the personalized increment by:

$$inc_{safe} = \max(\min(inc_{per}, inc_{inf}), inc_{sup}) \text{ in a safe range;}$$

and determining a clipped increment as an increment of a goal recommender.

11. The computer implemented method according to claim 10, further comprising defining, by the processor, the weekly goal as a sum of components of the user state related to a primary goal and the increment ($inc_{safe}$).

12. The computer implemented method according to claim 1, wherein a daily goal is determined by:

$$D_{i,j} = \min(\max(0, (W_i - P_{i,j})/(8 - j)), day_{sup}),$$

where $W_i$ is the weekly goal, $P_{i,j}$ is an accumulated amount of physical activity the user performed until day j, j is a value between 1 and 7, and $day_{sup}$ is a predetermined safe or beneficial threshold of daily activities, based on health guidelines.

13. The computer implemented method according to claim 12, further comprising:

comparing, by the processor, the amount of physical activities of a current day with a daily goal; and, in case the amount of physical activity of the current day is less than the daily goal, redistributing a remaining physical activity time by calculating the weekly goal and the amount of physical activities performed in a present week until the current day and equally distributing a difference throughout remaining days of the week.

14. The computer implemented method according to claim 1, wherein the method further comprises:

selecting, by the processor, a progression strategy with basis on a user classification; and determining, by the processor, a primary goal and a secondary weekly goal with basis on the progression strategy, wherein the primary goal is a numeric goal of active time or moderate time defined with basis on the user historical data, and a secondary goal a numeric goal of active or moderate time with a same value as a corresponding active time or moderate time of the user state.

15. The computer implemented method according to claim 1, wherein variables that define which is the primary goal and a secondary goal are inverted in case the user fails to follow a primary recommendation.

16. The computer implemented method according to claim 1, further comprising generating, by the processor, a message to send the goal recommendation to the user.

17. The computer implemented method according to claim 16, wherein the message is one of:

a recommendation informing the goal and suggestions of physical activity for a day or a week;

a reminder informing that part of the goal needs to be completed;

a modification providing feedback regarding a failure to follow the recommendation; and a reward providing feedback regarding a success to follow the recommendation.

18. The computer implemented method according to claim 16 or 17, further comprising:

determining, by the processor, the time for creating and sending the message to the user based on user information, wherein the user information comprises a user wake up time, a user bedtime, an active time and a moderate time of the user historical data, the goal recommendation, and a current time and date; and selecting a message template for creating the message with basis on message templates stored in a database of message templates.

19. The computer implemented method according to claim 1, further comprising:

determining, by the processor, maintenance goals recommendations comprising a maintenance goal for active time, $AT_m$, and a maintenance goal for moderate time, $MT_m$, wherein maintenance goals for the active time and for the moderate time are respectively defined as the active time and the moderate time of the user state calculated at a beginning of a week;

wherein recommended goals are limited to values of the maintenance goals for the active time and for the moderate time;

wherein based on the active time and the moderate time of the user state being below the maintenance goals for active time and for moderate time, the user is guided to achieve, progressively, the maintenance goals using normal rules of the method; and based on a current primary goal being equal to or greater than a corresponding maintenance goal and a secondary goal is lower than a corresponding maintenance goal, a change of strategy is applied to a current user type.

20. A system of generating physical activity recommendations characterized by comprising:

a processor; and a memory storing therein computer readable instructions that, when executed by the processor, cause the processor to perform the method as defined in claim 1.

21. A non-transitory computer-readable storage medium comprising computer-readable instructions, when executed by a processor, cause a computer to perform the method of claim 1.

* * * * *